(12) United States Patent
Norberg

(10) Patent No.: US 6,291,167 B1
(45) Date of Patent: Sep. 18, 2001

(54) METHOD FOR DETERMINING THE EXISTENCE OF A MUTATION

(75) Inventor: Torbjörn Norberg, Uppsala (SE)

(73) Assignee: Amersham Pharmacia Biotech AB, Uppsala (SE)

( * ) Notice: Subject to any disclaimer, the term of this patent is extended or adjusted under 35 U.S.C. 154(b) by 0 days.

(21) Appl. No.: 09/068,623
(22) PCT Filed: Nov. 7, 1996
(86) PCT No.: PCT/SE96/01432
§ 371 Date: Oct. 16, 1998
§ 102(e) Date: Oct. 16, 1998
(87) PCT Pub. No.: WO97/17467
PCT Pub. Date: May 15, 1997

(30) Foreign Application Priority Data

Nov. 10, 1995 (SE) .................................................... 9503991

(51) Int. Cl.⁷ .............................. C12Q 1/68; C12P 19/34; C07H 21/04; C07H 21/02
(52) U.S. Cl. .......................... 435/6; 435/91.1; 435/283.1; 435/287.1; 435/287.2; 536/23.1; 536/25.4
(58) Field of Search ......................... 435/6, 287.1, 287.2, 435/283.1, 91.1; 536/23.1, 25.4

(56) References Cited

U.S. PATENT DOCUMENTS 5,108,179 * 4/1992 Myers .................................. 356/344
5,552,322 * 9/1996 Nemoto et al. .................... 435/287.2

* cited by examiner

Primary Examiner—Jeffrey Fredman
Assistant Examiner—BJ Forman
(74) Attorney, Agent, or Firm—Royal N. Ronning, Jr.

(57) ABSTRACT

In a method for determining the existence of a mutation in a nucleic acid fragment from an electrical signal generated by a DNA sequencer made up of sequence information produced by fluorescent fragment products of different lengths of said nucleic acid fragment, followed by a run-off peak produced by fluorescent full length fragment products of said nucleic acid fragment, any difference between said run-off peak and a reference run-off peak generated by unmutated full length fragment products of said nucleic acid fragment, is determined, a difference indicating the existence of a deletion or insertion mutation.

3 Claims, 1 Drawing Sheet

Sequence region    Run-off region a)

b)

c)

METHOD FOR DETERMINING THE EXISTENCE OF A MUTATION

This is a 371 of PCT/SE96/01432, filed Nov. 07, 1996.

TECHNICAL FIELD

The invention relates to a method and an apparatus for determining the existence of a mutation in a nucleic acid fragment from an electric signal generated by a DNA sequencer and made up of sequence information produced by fluorescent fragment products of different lengths of said nucleic acid fragment, followed by a run-off peak produced by fluorescent full length fragment products of said nucleic acid fragment.

BACKGROUND OF THE INVENTION

DNA sequencing, i.e. determining the sequence of nucleotides in a gene or in a segment of DNA, commonly involves several sequential steps aimed at:

Isolating genetic material from biological material.

Amplifying the gene of interest using polymerase chain reaction (PCR) so that sufficient material of the gene of interest is available for sequence analysis.

Performing sequencing reactions using the principles of Sanger. This step enzymatically generates a large number of differently elongated complementary copies of the gene. By introduction of base specific elongation terminators, each elongated copy of the gene will terminate with a specific type of nucleotide. Each reaction corresponds to one specific type of nucleotide, Adenine (A), Thymine (T), Guanine (G) or Cytosine (C), i.e. only one type of elongation terminator, will be incorporated in each reaction. To enable detection of these elongated gene copies, a fluorescently labelled molecule is introduced in the gene copy during the enzymatic reaction. Thus, all elongated gene copies will be fluorescently labelled to facilitate their detection.

Separating the mixture of differently elongated complementary copies of the gene according to their molecular size using gel electrophoresis.

Sequentially detecting the differently elongated complementary copies of the gene, separated according to molecular size during gel electrophoresis, using a DNA sequencer system, e.g. the DNA sequencer marketed under the trademark ALF by Pharmacia Biotech AB, Uppsala, Sweden. During the electrophoresis, any fluorescent molecules passing a perpendicularly oriented laser beam, will be activated and the fluorescence from each molecule will be detected by light sensitive detectors, each representing one type of nucleotide in the sample.

Determining the nucleotide sequence by superimposing the signals from four detectors representing the four different nucleotides of the sample gene.

An example of such signals obtained from four such detectors is shown in FIG. 1 on the appended drawing. As apparent, the diagram in FIG. 1 is divided into a sequence region, containing sequence data, and a run-off region, containing the so called "run-off peak" which is described more in detail below.

Sequence data obtained by processing and sequencing DNA samples from tumour tissue in an automatic sequencer, can be used to detect inherited or induced mutations in genes related to the occurrence or progression of the tumour. When mutated, the sample sequence obtained from the sequencer will often consist of a mixture of two superimposed sequence components, namely the wild type component and a mutated component. This could be due either to a mixture of two cell populations in the sample or to a mutation in one of the two copies of the gene, if both are present in the sample. In cases where the mutated sequence component is the predominant component, insertion and deletion mutations as well as point mutations can be readily detected by aligning the sequence data obtained from the sample with the expected wild type sequence using standard alignment algorithms (see e.g. S. Needleman and C. Wunsch, J. Mol. Biol. 48, 444 (1970)), and W. R. Pearson and W. Miller, Methods in Enzymology, 210, 575 (1992)). Often, however, the mutated sequence material is mixed up with an equally large amount of non-mutated material. In some cases, the non-mutated material will even be predominant. In these cases ordinary alignment algorithms fail to resolve the mutation.

BRIEF DESCRIPTION OF THE INVENTION

The object of the invention is to bring about a simple and reliable method of determining the existance of a mutation in a nucleic acid fragment.

In the method according to the invention for determining the existence of a mutation in a nucleic acid fragment from an electric signal generated by a DNA sequencer and made up of sequence information produced by fluorescent fragment products of different lengths of said nucleic acid fragment, followed by a run-off peak produced by fluorescent full length fragment products of said nucleic acid fragment, this is attained, mainly, by determining any difference between said run-off peak and a reference run-off peak generated by unmutated full length fragment products of the nucleic acid fragment, a difference indicating the existence of a deletion or insertion mutation.

This object is also attained by the apparatus according to the invention for determining the existence of a mutation in a nucleic acid fragment from an electric signal generated by a DNA sequencer and made up of sequence information produced by fluorescent fragment products of different lengths of said nucleic acid fragment, followed by a run-off peak produced by fluorescent full length fragment products of said nucleic acid fragment, mainly, in that it comprises means for determining any difference between said run-off peak and a reference run-off peak generated by unmutated full length fragment products of said nucleic acid fragment, a difference indicating the existence of a deletion or insertion mutation.

BRIEF DESCRIPTION OF THE DRAWING

The invention will be described more in detail below with reference to the appended drawings

PREFERRED EMBODIMENTS

When separating fluorescent DNA fragments of limited size in an electrophoresis gel and exciting these fragments to fluoresce, e.g. in the case of direct sequencing of PCR fragments, full length fragment products exist where the polymerase have not incorporated any chain terminators. This results in the presence of a prominent peak, the so called "run-off peak", in all raw data signal curves from a sequencer. This run-off peak is located at the end of the actual sequence information.

Figure 1:
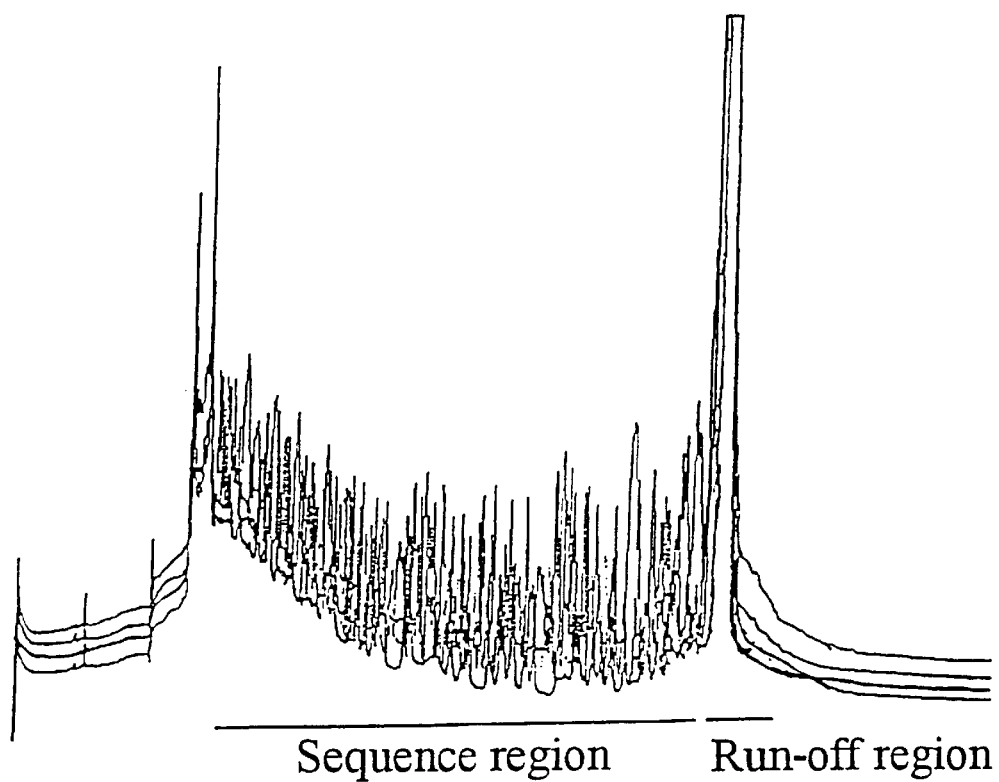
FIG. 1 depicts the trace of an electrical signal produced by a DNA sequencer, depicting the Sequence region and the Run-off region.
Figure 2:
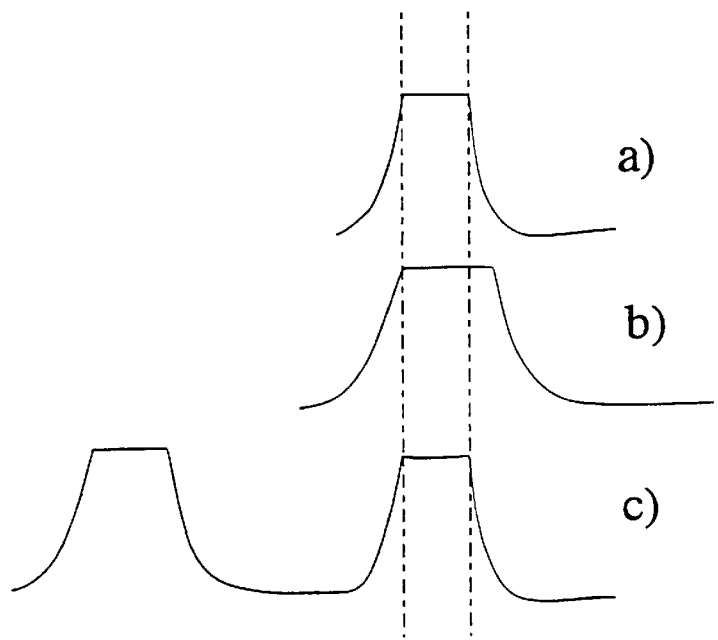
FIG. 2a schematically shows a normal run-off peak.
FIG. 2b schematically shows a broadened run-off peak.
FIG. 2c schematically shows a split run-off peak.

An example of a normal run-off peak generated by unmutated full length fragment products of a nucleic acid fragment, is schematically shown in FIG. 2a. The run-off peak in FIG. 2a may correspond to the run-off peak in the run-off region shown in FIG. 1.

If two species of DNA fragments are present in the sequencing reaction, e.g. one from a tumour tissue and one from surrounding normal tissue, they will generate one run-off peak each.

If the DNA fragments are of equal size, these two run-off peaks will, of course, coincide.

However, in case of a deletion or insertion mutation in one of the fragments, the fragments will differ in size and two separate run-off peaks will be generated.

A small deletion or insertion will result in a broadening of the run-off peak.

Such a broadened run-off peak originating from a small insertion mutation, is schematically shown in FIG. 2b. As apparent from FIG. 2b, the normal "unmutated" run-off peak of FIG. 2a has been broadened, so that the run-off peak of FIG. 2b ends after the run-off peak of FIG. 2a.

In case of a large deletion mutation, a split run-off peak will be generated as shown in FIG. 2c. As apparent from FIG. 2c, the normal "unmutated" run-off peak coincides with the normal "unmutated" run-off peak of FIG. 2a, while the run-off peak from the fragments in which a large deletion mutation is present, will appear before the normal "unmutated" run-off peak.

The indication of insertion and deletion mutations based on the run-off peak behaviour, is very sensitive and a contribution of less than 5% mutated material can be readily detected. The resolution in size difference between the two fragments is however limited to about ±2 bases. This is of course dependent on the resolution of the electrophoresis gel.

It should be understood, however, that when using the run-off peak information alone for the mutation assignment, no information about the localization of the mutation along the DNA fragment will be achievable.

The run-off peak information is a sensitive means for the mutation detection and may be used as a consistency check of the mutation assignment derived from sequence data.

In accordance with the invention, any difference between a run-off peak generated by mutated full length fragment products, such as the run-off peak shown in FIG. 2b, and a normal "unmutated" run-off peak or reference run-off peak generated by unmutated full length fragment products, such as the run-off peak shown in FIG. 2a, is determined as an indication of the existence of a mutation.

In accordance with a first embodiment of the method according to the invention, the difference between the peak width of the run-off peak in FIG. 2b and the peak width of the run-off peak in FIG. 2a, is measured in view of the fact that the size of the peak width difference is directly proportional to the size of the mutation.

If, as in FIG. 2b, the wider peak ends after the normal peak of FIG. 2a, this is an indication of an insertion mutation.

However, should the wider run-off peak begin before the run-off peak of FIG. 2a, this is an indication of a deletion mutation.

In accordance with a second embodiment of the method according to the invention, the difference between the run-off peaks in FIGS. 2a and 2b may be determined by measuring any difference between the location of the peak centers of these run-off peaks.

The peak center of the run-off peak of FIG. 2b is located after the center of the run-off peak of FIG. 2a. This is then an indication of an insertion mutation.

If, as in FIG. 2c, the center of the "mutated" run-off peak is located in front of the center of the normal or reference run-off peak, this indicates the prescence of a deletion mutation.

The size of the difference between the peak centers is directly proportional to the size of the mutation.

As should be apparent from the above, the method according to the invention is a simple and reliable method of determining not only the existence of a mutation in a nucleic acid fragment but also whether the mutation is a deletion mutation or an insertion mutation.

The apparatus (not shown) according to the invention for determining the existence of a mutation in a nucleic acid fragment from an electric signal generated by a DNA sequencer and made up of sequence information produced by fluorescent fragment products of different lengths of said nucleic acid fragment, followed by a run-off peak produced by fluorescent full length fragment products of said nucleic acid fragment, comprises means (not shown) for determining any difference between said run-off peak and a reference run-off peak generated by unmutated full length fragment products of said nucleic acid fragment, a difference indicating the existence of a deletion or insertion mutation.

In a first embodiment of the apparatus according to the invention, the means (not shown) for determining any difference between said run-off peak and said reference run-off peak, is adapted to measure any difference in peak width between these run-off peaks, a wider run-off peak ending after said reference run-off peak, indicating an insertion mutation, while a wider run-off peak beginning before said reference run-off peak indicating a deletion mutation, the size of the peak width difference being directly proportional to the size of the mutation.

In a second embodiment of the apparatus according to the invention, the means (not shown) for determining any difference between said run-off peak and said reference run-off peak, is adapted tp measure any difference between the location of the centers of these run-off peaks, a location of the center of said run-off peak in front of the center of said reference run-off peak indicating a deletion mutation, a location of the center of said run-off peak after the center of said reference run-off peak indicating an insertion mutation, the size of said difference being directly proportional to the size of the mutation.

The apparatus according to the invention is preferably implemented in computer software.

What is claimed is:

1. In a method for determining the existence of a mutation in a nucleic acid fragment from an electric signal generated by a DNA sequencer and made up of sequence information produced by fluorescent fragment products of different lengths of said nucleic acid fragment, followed by a run-off peak produced by fluorescent full length fragment products of said nucleic acid fragment, wherein the improvement comprises determining any difference between said run-off peak and a reference run-off peak generated by unmutated full length fragment products of said nucleic acid fragment, a difference indicating the existence of a deletion or insertion mutation.

2. Method according to claim 1, characterized in that said difference between said run-off peak and said reference run-off peak is determined by measuring any difference in peak width between these run-off peaks, a wider run-off peak ending after said reference run-off peak, indicating an insertion mutation, while a wider run-off peak beginning before said reference run-off peak indicating a deletion mutation, the size of the peak width difference being directly proportional to the size of the mutation.

3. Method according to claim 1, characterized in that said difference between said run-off peak and said reference run-off peak is determined by measuring any difference between the location of the centers of these run-off peaks, a location of the center of said run-off peak in front of the center of said reference run-off peak indicating a deletion mutation, a location of the center of said run-off peak after the center of said reference run-off peak indicating an insertion mutation, the size of said difference being directly proportional to the size of the mutation.

* * * * *